United States Patent [19]

Mannix et al.

[11] Patent Number: 5,334,384
[45] Date of Patent: Aug. 2, 1994

[54] PROCESS FOR PURIFICATION OF STREPTAKINASE USING A REDUCING AGENT

[75] Inventors: Christopher J. Mannix; Richard A. G. Smith; Ceri J. Lewis, all of Epsom; Julian S. Harber, Worthing, all of England

[73] Assignee: Beecham Group p.l.c., United Kingdom

[21] Appl. No.: 422,430

[22] Filed: Oct. 17, 1989

[30] Foreign Application Priority Data

Oct. 19, 1988 [GB] United Kingdom ............. 8824496.7

[51] Int. Cl.$^5$ ...................... C12N 1/02; A61K 37/547
[52] U.S. Cl. ................................. 424/94.63; 424/94.1; 424/94.64; 435/212; 435/216; 435/814; 435/815; 435/885; 514/822
[58] Field of Search ............... 435/216, 226, 212, 219, 435/815, 814, 885; 424/94.64, 94.63, 94.1; 514/822

[56] References Cited

U.S. PATENT DOCUMENTS

| | | | |
|---|---|---|---|
| 2,784,145 | 3/1957 | Ablondi et al. | 435/216 |
| 3,226,304 | 12/1965 | Siiteri et al. | 435/216 |
| 3,255,094 | 6/1966 | Mather et al. | 435/216 |
| 3,419,472 | 12/1968 | Siiteri | 435/194 |
| 3,444,045 | 5/1969 | Derenzo et al. | 435/216 |

OTHER PUBLICATIONS

Brocklehurst K et al. Biochem J. vol. 133, 593–584 (1973).
Eur. J. Biochem. 44 189–194 (1974).
Infection and Immunity 55 u 12 pp. 3225–3227.
Tomar Chem Abstracts 84 (1976) Abstract #84:41761b.
E. C. de Renzo, et al., "Preparation and Certain Properties of Highly Purified Streptokinase", The Journal of Biological Chemistry, vol. 242, No. 3, Feb. 10, pp. 533–542, 1967.
Monica Einarsson, et al., "Characterization of Highly Purified Native Streptokinase and Altered Streptokinase After Alkaline Treatment", Biochimica et Biophysica Acta, 568 (1979) 19–29.
Brocklehurst et al., Preparation of Fully Active Papain from Dried Papaya Latex, Biochem, J. (1973) 133, pp. 573–584.
Kehoe et al., Nucleotide . . . Toxins, Infection and Immunity, Dec., 1987, pp. 3228–3232.
Jackson et al., "Complete Amino Acid . . . Proteases," Biochemistry, 1982, vol. 21, pp. 6620–6625.

Primary Examiner—Michael G. Wityshyn
Assistant Examiner—Jane Williams
Attorney, Agent, or Firm—Rosenman & Colin

[57] ABSTRACT

A process for the separation of streptokinase from contaminating proteins in a streptokinase-containing mixture, which comprises treating the mixture with a reducing agent to reduce disulphide bridges in the contaminating proteins to free thiol groups, contacting the mixture with a reagent R-X wherein R is a group capable of reacting with a free thiol group and X is a group $R^1$ capable of reacting with a free thiol group or is a thiol-containing matrix, and thereafter separating the resulting chemically modified contaminating proteins from the mixture to provide streptokinase in a form substantially free of contaminating proteins.

10 Claims, No Drawings

PROCESS FOR PURIFICATION OF STREPTAKINASE USING A REDUCING AGENT

This invention relates to a process for the purification of streptokinase.

Streptokinase is an extracellular protein produced by various strains of streptococci. Its activity was first reported by W. S. Tillet and R. L. Garner (1933) J. Exp. Med. 58 485–502, who discovered that this protein caused the lysis of blood clots. It is now well established that the fibrinolytic activity of streptokinase originates in its ability to activate plasma plasminogen (F. J. Castellino (1979) Trends Biochem. Sci. (Pers. Ed.) 4, 1–5).

Streptokinase is used clinically as an intravenous thrombolytic agent for the treatment of acute myocardial infarction (see Gruppo Italiano per lo studio della streptochinase nel infarto Miacardico (GISSI) (1986) Lancet, 387). It is also one of the two protein components of the thrombolytic agent known as APSAC (anisoylated plasminogen streptokinase activator complex) described in EP-A-0028489.

Streptokinase is produced by certain Streptococci and certain bacteria which contain appropriate genetic material derived from Streptococci of Lancefield groups A, C or G. Streptokinase which is to be used for clinical purposes is commonly prepared from cultures of *S. equisimilis* strain H46A.

Numerous methods of purifying streptokinase have been described which are based on quantitative differences in solubility, electrical charge, molecular size and shape or non specific physical interactions with surfaces. Published methods often result in unacceptable losses of streptokinase or inadequate removal of impurities and employ expensive harsh or flammable reagents.

Streptokinase, unlike the contaminating proteins which make up the impurities, such as streptolysin or streptodornase, does not contain the amino acids cysteine or cystine (Einarsson et al (1979) Biochim, Biophys. Acta 568, 19–29; De Renzo et al (1967) J. Biol. Chem. 242, 533–542). This structural difference may be employed to provide a more effective method for the purification of streptokinase from the fermentation broth.

According to the present invention there is provided a process for the separation of streptokinase from contaminating proteins in a streptokinase-containing mixture, which comprises treating the mixture with a reducing agent to reduce disulphide bridges in the contaminating proteins to free thiol groups, contacting the mixture with a reagent R-X wherein R is a group capable of reacting with a free thiol group and X is a group $R^1$ capable of reacting with a free thiol group or is a thiol-containing matrix, and thereafter separating the resulting chemically modified contaminating proteins from the mixture to provide streptokinase in a form substantially free of contaminating proteins.

The purified streptokinase will preferably conform to the purity specification of the European Pharmacopoeia and will preferably comprise less than 1 IU streptodornase/10,000 IU streptokinase and less than 1 IU streptolysin/1,000,000 IU streptokinase.

The reduction of the disulphide bridges may be carried out with any suitable reducing agent. Examples include thiols with low redox potentials, such as dithiothreitol (DTT) and dithioerythritol, either alone or coupled to a secondary reducing agent, such as NADPH (Lou M. F. Methods in Enzymology 143 p124 Academic Press 1987). Certain borohydrides such as sodium borohydride or cyanoborohydride may also be used, as may electrochemical reduction (Kadin H. Methods in Enzymology 143 p 256 Acad. Press 1987). Further methods of protein reduction will be apparent from the review of Jocelyn, P. C. (Meth. Enz. 143 p 246 Academic Press 1987). Of these methods treatment with dithiothreitol is preferred, preferably at a DTT concentration of 5–100 mM, more preferably 25–100 mM, pH 6.0–8.5 and temperature 5°–35° C.

Suitable examples of the groups R and $R^1$ include
5-nitro-2-pyridylthio
5-carboxy-2-pyridylthio
2-pyridylthio
4-pyridylthio
2-benzothiazolylthio
4-nitro-3-carboxyphenylthio
and the N-oxides of the above pyridyl groups.

Suitable matrices for use in the process of the invention incorporate those particulate insoluble hydrophilic materials which may be used as matrices in various forms of protein chromatography, notably modified agarose, dextran and silica and which have been modified to incorporate thiol groups, as described for example in GB Patent No. 1506403 or 1597757, or which have been formed by polymerization of monomers which include thiol compounds. Examples of such materials are described by Brocklehurst, K et al (1973) *Biochem J.* 133, 573–584 and sold under the names of Affigel 401 sulphydryl gel by Biorad Inc and Thiopropyl-Sepharose 6B or Agthiol Agarose-Ether-Thiol by Pharmacia Ltd.

The thiol groups on the matrix may most effectively be linked to the matrix by means of spacer groups which facilitate contact with the thio groups within the reduced proteins. Matrix linker thiol groups with carboxylate or amino groups adjacent to the thiol are particularly suitable. An example of such a preferred material is cysteine or glutathione immobilized to sepharose.

A preferred reagent $R-R^1$ is 2,2'-dipyridyldisulphide, which is sold by Aldrich Chemical Co. under the trade name of Aldrithiol-2.

The streptokinase mixture is preferably separated from the fermentation broth prior to purification in accordance with the invention by a technique such as centrifugation, filtration or adsorption which permits separation of the streptokinase from the bacterial cells. Such separation is preferably combined with a further purification step in which streptokinase is freed of gross contamination with thiol containing impurities. Suitable techniques for pre-treatment of broths include fractional precipitation, Florisil and ion exchange chromatography, for example as described in East German Patent Nos. 126342 and 121522, De Renzo E. C. (1967) J. Biol. Chem. 242, 533 or U.S. Pat. No. 2,784,145. Preferred treatments are chromatographic in nature and avoid exposure to reagents which may modify streptokinase.

Separation of the chemically modified contaminating proteins may be carried out physically and/or chemically.

Where the reagent is of the form $R-R^1$, the reaction thereof with the streptokinase mixture will provide mixed disulphides of the groups R and $R^1$ and the reduced impurities of the mixture. The reaction, under most conditions, results in the precipitation of the resulting chemically modified contaminating proteins.

The conditions surrounding this precipitation step may be controlled so as to maximize the formation of the precipitate.

In particular, the preferred concentration of reagent R-R[1] is 10-200 mM and the activation is preferably carried out at pH 6.0-8.5 and temperature 5°-35° C.

The precipitate may be removed from the mixture by any suitable conventional physical procedure, for example filtration, sedimentation, centrifugation or retention of the precipitate within a chromatographic column or other suitable device.

Filtration may be effected by use of any suitable filter, preferably capable of retaining particles of size 1 μm or less. Suitable materials include glass fiber, polysulphone, polyvinylidene difluoride and nylon.

Where the precipitation has been optimized, the separation from the mixture by filtration may result in streptokinase of the required degree of purity. Where the required degree of purity has not been achieved, however, the filtrate itself may be applied to a thiol-containing matrix to remove residual contaminating protein by thiol exchange chromatography.

Alternatively, in particular where incomplete precipitation has occurred, the mixture may be applied directly to the thiol-containing matrix without prior filtration.

At low contaminant concentrations (for example, less than 25 IU/ml), precipitation may not be effective and the matrix method may advantageously be employed.

Where the reagent is of the form R-X where R is as previously defined and X is a thiol-containing matrix, the process of the invention essentially involves contacting the reduced mixture with an activated thiol-containing matrix.

Activation of the thiol-containing matrix may be achieved by treating the matrix with a reagent R-R[1] where R and R[1] are as previously defined, to provide mixed disulphides of the groups R and R[1] and the thio matrix. A preferred reagent is Aldrithiol-2 which may be used to prepare thio matrix 2-pyridyl disulphides suitable for reaction with reduced streptokinase mixtures. Such thio matrix 2-pyridyl disulphides may also be prepared by alternative means such as those described in GB 1 506 409 and may be used in place of those prepared from the thio matrix.

In one aspect the invention thus provides a process for the separation of streptokinase from contaminating proteins in a streptokinase-containing mixture, which comprises treating the mixture with a reducing agent to reduce disulphide bridges in the contaminating proteins to free thiol groups, contacting the mixture with a matrix comprising immobilized thiol-containing compounds, wherein one of the reduced mixture and matrix are activated prior to contact, and eluting streptokinase from the matrix in a form substantially free of contaminating proteins.

The streptokinase may conveniently be separated from the matrix by washing with an aqueous buffer which is conveniently designed to minimize any non-covalent interaction between streptokinase and the matrix. Buffers containing at least 200 mM sodium ions and optionally a chelating agent such as EDTA have been found suitable.

After separation of the streptokinase, the matrix may be treated with a reducing agent, such as those described hereinbefore, before washing with an aqueous buffer to regenerate the column for re-use.

The matrix is conveniently provided in the form of a column, and the purification may be performed in a batchwise or continuous way.

The purification of streptokinase according to the invention is now described using the following materials and methods.

EXAMPLES OF STREPTOKINASE PURIFICATION MATERIALS AND METHODS

Materials

Sepharose 4B was obtained from Pharmacia LKB, Uppsala, Sweden. Thiohydroxypropyl and glutathione agaroses were also obtained from Pharmacia or were synthesized. 2,2'dipyridyl disulphide (Aldrithiol-2) was obtained from Aldrich Chemical Company, Gillingham, Dorset. Other fine chemicals were obtained from Sigma (London) Chemical Co., Poole, Dorset, UK, or Fisons, Loughborough, Leics. UK.

Methods

1. Covalent Chromatography (a) Pretreatment of streptokinase-containing protein solutions i) Protein solution was reduced with 25 mM DTT and incubated at 30° C. for 30 min. Excess DTT was removed either by buffer exchange using G-25 chromatography on Pharmacia PD-10 columns or buffer exchange by diafiltration in an Amicon stirred cell ultrafiltration system. In both cases protein solution was exchanged into degassed 150 mM NaCl, 100 mM $NaH_2PO_4$, 1 mM EDTA, pH 7.0 buffer.

ii) Protein solutions were reduced with 25 mM DTT and incubated at 30° C. for 30 min. with gentle agitation. (Protein solution was at this point in 10 mM $NaH_2PO_4$, 200 mM NaCl pH 7.0 buffer). Aldrithiol-2 (2,2'dipyridyl disulphide) was added to a final concentration of 50 mM. Excess Aldrithiol-2 was then removed by one of the two methods outlined above.

(b) Chromatography

Covalent chromatography was performed by one of the two following methods: by method A) (in the case of streptokinase pretreatment method (i) or by method B) (in the case of pretreatment method ii).

A) 20 ml of glutathione agarose or hydroxy thiopropyl agarose was loaded as a 50% slurry into a Pharmacia C-16 chromatography column. The column was then washed with 150 mM NaCl, 1 mM EDTA 100 mM $NaH_2PO_4$ pH 7.0 (Buffer A) at a flow rate of 20 cm. $h^{-1}$ until a stable packed bed was obtained. 100 ml of 50 mM DTT was then passed through the column at a superficial flow rate of 10 cm. $h^{-1}$ to ensure total reduction of the thiol agarose. The column was then washed with degassed buffer A until completely free of DTT. (10 column volumes). The column was then washed with a saturated solution of Aldrithiol-2 at a superficial flow rate of 10 cm. $h^{-1}$. (100 ml) and again washed with degassed buffer A until free of Aldrithiol-2.

The protein solutions prepared by method i) (volume 10-20 ml) were loaded onto the column at a flowrate of 10 cm. $h^{-1}$ and washed with buffer A. The column was monitored at 280 nm and the washed protein peak retained and assayed. The column could then be regenerated by the method outlined previously.

B) 20 ml of glutathione agarose or hydroxy thiopropyl agarose was loaded as a 50% slurry into a Pharmacia C-16 chromatography column. The column was then washed with 150 mM NaCl, 1 mM EDTA, 100 mM NaH$_2$PO$_4$ pH 7.0 (Buffer A) at a flow rate of 20 cm. h$^{-1}$ until a stable packed bed was obtained. 100 ml of 50 mM DTT was then passed through the column at a flow rate of 10 cm. h$^{-1}$ to ensure total reduction of the thiol agarose. The column was then washed with degassed buffer A until completely free of DTT. (10 column volumes).

Protein solution prepared by method ii) (volume 20-100ml) was loaded onto the column at a flowrate of 10 cm. h$^{-1}$ and washed with buffer A. The column was monitored at 280 nm and the washed protein peak retained and assayed. The column could then be regenerated by the method outlined previously.

2. Covalent precipitation (Method C)

(a) Pretreatment of streptokinase-containing protein solution

Protein solution was reduced with 100 mM DTT and incubated at 30° C. for 30 minutes. Aldrithiol-2 to a final concentration of 150mM was then added and the solution (at pH 7.5) incubated with agitation for 20 min at 30° C. followed by 15 min at 35° C. The solution was then cooled to 5° C. and held for 20 min.

(b) Removal of precipitate

Residual Aldrithiol-2 and precipitated protein contaminants were removed by either (i) Filtration through Whatman glass microfibre GF/A prefilter (pore size 1.6 μm) followed by a whatman glass microfibre GF/F final filter (pore size 0.7 μm) under vacuum in a buchner filter system and the filtrate retained and assayed; or (ii) Centrifugation at 6000×g for 20 min at 5° C. The supernatant was then decanted from the precipitate, retained and assayed.

Assay

Samples under test were serially diluted tenfold with phosphate buffered saline to give the following dilutions:

1, 0.1, 0.01 and 0.001.

These diluted samples were then assayed for streptolysin-O by an adaptation of the European Pharmacopoea method, which entails using 1/5 the volumes of sample and reagents quoted in the European Pharmacopoea 2nd Edition 356-3 (1984). The procedure was repeated with intermediate dilutions of the samples.

The results are summarized in the following Table.

Discussion

All methods (methods A, B and C) give high yields of streptokinase (80-100%) and all offer significant reduction in the levels of streptolysin.

Method A leaves detectable levels of streptolysin in the solution. In the case of method B, due to the lower concentration of streptokinase, streptolysin levels were below the sensitivity of the assay, hence the results are quoted as "less than". In the case of Method B, Run 1, the level of streptokinase was insufficient to determine whether the sample passed or failed the European Pharmacopoeia standard. Low levels of streptolysin are detectable in material produced by method C but these are within the specification of the European Pharmacopoeia. Method C is preferred where it is required to produce material to European Pharmacopoeia standards of purity without the cost of utilizing thiol matrices.

We claim:

1. A process for the separation of streptokinase from contaminating proteins containing reducible disulphide bridges in a streptokinase-containing mixture, which comprises treating the mixture with a reducing agent to reduce said disulphide bridges in the contaminating proteins to free thiol groups, contacting the mixture with a reagent R-X wherein R is a group capable of reacting with a free thiol group and X is a group R$^1$ capable of reacting with a free thiol group or is a thiol-containing matrix, and thereafter separating the resulting chemically modified contaminating proteins from the mixture to provide streptokinase in the form substantially free of said contaminating proteins.

2. A process according to claim 1 in which the reducing agent is dithiothreitol.

3. A process according to claim 1 in which the groups R and R$^1$ are selected from
5-nitro-2-pyridylthio
5-carboxy-2-pyridylthio
2-pyridylthio
4-pyridylthio
2-benzothiazolylthio
4-nitro-3-carboxyphenylthio
and the N-oxides of the above pyridyl groups.

4. A process according to claim 1 in which the reagent R-X is of the form R-R$^1$.

5. A process according to claim 4 in which the reagent R-R$^1$ is 2,2'-dipyridyldisulphide.

6. A process according to claim 4 which the concentration of the reagent R-R$^1$ is 10-200 mM.

7. A process according to claim 4 in which the reaction of the reduced mixture with the reagent R-R$^1$ is carried out at pH 6.0-8.5.

TABLE

| Method | Run number | Load Streptokinase (mg) | Load Streptolysin (IU/10 mg SK) | Eluate Streptokinase (mg) | Eluate Streptolysin (IU/10 mg SK) | Yield (SK) % |
|---|---|---|---|---|---|---|
| A | 1 | 131.0 | 1050 | 114 | 18.0 | 87 |
|   | 2 | 114.0 | 5405 | 95 | n.d. | 83 |
|   | 3 | 70.0 | 670 | 69 | 1.3 | 102 |
| B | 1 | 69.0 | 4370 | 68 | <3.00 | 102 |
|   | 2 | 272.0 | 6820 | 256 | <0.19 | 92 |
|   | 3 | 293.0 | 2940 | 243 | <0.87 | 87 |
|   | 4 | 270.0 | 8160 | 224 | <0.54 | 83 |
| C | 1 | 6240 | 2080 | 6178 | 0.36 | 99 |
|   | 2 | 2750 | 90 | 2668 | 0.68 | 97 |

[1] mg SK is nominally 100,000 IU SK

8. A process according to claim 4 in which the reaction of the reduced mixture with the reagent R-R$^1$ is carried out at a temperature of 5°–35° C.

9. A process according to claim 4 in which the resulting chemically modified contaminating proteins form a precipitate which is separated by filtration, sedimentation, centrifugation or by retention within a chromatographic column.

10. A process according to claim 9 in which residual chemically modified contaminating proteins are removed by thiol exchange chromatography.

* * * * *